(12) United States Patent
Hussein et al.

(10) Patent No.: US 12,060,504 B2
(45) Date of Patent: Aug. 13, 2024

(54) HOT MELT ADHESIVE FOR CONSTRUCTION OF DISPOSABLE NONWOVEN HYGIENE PRODUCT

(71) Applicant: BOSTIK SA, Colombes (FR)

(72) Inventors: Naji Hussein, Venette (FR); Stéphanie Komar, Venette (FR); Bénédicte Delory, Venette (FR); Magali Mangeant, Venette (FR)

(73) Assignee: BOSTIK SA, Colombes (FR)

( * ) Notice: Subject to any disclaimer, the term of this patent is extended or adjusted under 35 U.S.C. 154(b) by 478 days.

(21) Appl. No.: 17/415,781

(22) PCT Filed: Dec. 4, 2019

(86) PCT No.: PCT/EP2019/083675
§ 371 (c)(1),
(2) Date: Jun. 18, 2021

(87) PCT Pub. No.: WO2020/126506
PCT Pub. Date: Jun. 25, 2020

(65) Prior Publication Data
US 2022/0056309 A1 Feb. 24, 2022

(30) Foreign Application Priority Data
Dec. 20, 2018 (EP) .................................... 18306755

(51) Int. Cl.
| | | |
|---|---|---|
| C09J 5/06 | (2006.01) | |
| A61L 15/58 | (2006.01) | |
| B32B 5/02 | (2006.01) | |
| B32B 7/12 | (2006.01) | |
| B32B 27/12 | (2006.01) | |
| B32B 27/32 | (2006.01) | |
| B32B 37/12 | (2006.01) | |
| B32B 37/20 | (2006.01) | |
| C09J 11/08 | (2006.01) | |
| C09J 123/08 | (2006.01) | |
| C09J 123/14 | (2006.01) | |

(52) U.S. Cl.
CPC ................ *C09J 5/06* (2013.01); *B32B 5/022* (2013.01); *B32B 7/12* (2013.01); *B32B 27/12* (2013.01); *B32B 27/32* (2013.01); *B32B 37/1207* (2013.01); *B32B 37/203* (2013.01); *C09J 11/08* (2013.01); *C09J 123/08* (2013.01); *C09J 123/142* (2013.01); *A61L 15/585* (2013.01); *B32B 2037/1215* (2013.01); *B32B 2250/02* (2013.01); *B32B 2250/246* (2013.01); *B32B 2255/10* (2013.01); *B32B 2255/26* (2013.01); *B32B 2262/0253* (2013.01); *B32B 2305/20* (2013.01); *B32B 2307/726* (2013.01); *B32B 2307/732* (2013.01); *B32B 2309/02* (2013.01); *B32B 2323/04* (2013.01); *B32B 2323/10* (2013.01); *B32B 2555/02* (2013.01); *C09J 2409/00* (2013.01); *C09J 2423/00* (2013.01); *C09J 2423/04* (2013.01); *C09J 2423/10* (2013.01); *C09J 2491/00* (2013.01)

(58) Field of Classification Search
CPC . C09J 5/06; C09J 11/08; C09J 2423/00; C09J 2423/04; C09J 2423/10; C09J 2409/00; C09J 123/14; C09J 123/08; C09J 123/142; C09J 7/30; C09J 2301/304; C08L 23/142; C08L 23/20; C08L 2205/03; A61L 15/585; B32B 5/022; B32B 27/12; B32B 27/32; B32B 7/12; B32B 37/1207; B32B 37/203; B32B 2307/1215; B32B 2307/726; B32B 2307/32; B32B 2250/02; B32B 2250/46; B32B 2255/10; B32B 2255/26; B32B 2255/02; B32B 2262/0253; B32B 2323/10

See application file for complete search history.

(56) References Cited

U.S. PATENT DOCUMENTS

| | | | |
|---|---|---|---|
| 9,109,143 B2 | 8/2015 | Tse et al. | |
| 2013/0202902 A1 | 8/2013 | DeJesus et al. | |
| 2017/0204306 A1 | 7/2017 | Wang et al. | |
| 2018/0186986 A1* | 7/2018 | Chen .................... | C08L 23/142 |

FOREIGN PATENT DOCUMENTS

| | | |
|---|---|---|
| JP | 2014514390 A | 6/2014 |
| WO | 2017177164 A1 | 10/2017 |

* cited by examiner

*Primary Examiner* — Camie S Thompson
(74) *Attorney, Agent, or Firm* — NK Patent Law

(57) ABSTRACT

1) Hot melt adhesive composition comprising: —from 30% to 55% of a composition (A) consisting of 2 copolymers of propylene and ethylene (A1) and (A2), with Mw of less than 100,000 Da, wherein: —(A1) is an essentially amorphous copolymer, with a DSC melt enthalpy of 10 less than 30 J/g; —(A2) is a semicrystalline copolymer with a DSC melt enthalpy of more than 30 J/g; and —the ratio:weight of (A2)/weight of (A1) is from 0.2 to 1.5; —from 20% to 50% of a tackifying resin (B); and 1 —from 2% to 25% of a plasticizer (C) consisting of a liquid polybutene oligomer. 2) Process of manufacturing an assembly product, preferably a disposable nonwoven absorbent article, implementing said hot melt adhesive composition.

15 Claims, No Drawings

HOT MELT ADHESIVE FOR CONSTRUCTION OF DISPOSABLE NONWOVEN HYGIENE PRODUCT

CROSS-REFERENCE TO RELATED APPLICATIONS

This application is a U.S. National Stage application of International Patent Application No. PCT/EP2019/083675, filed on Dec. 4, 2019, which claims the benefit of European Patent Application No. 18306755.2, filed on Dec. 20, 2018.

The present invention relates to a hot-melt adhesive composition which is suitable for a process of a laminate manufacturing, in particular of a disposable nonwoven hygiene product manufacturing, and which is more particularly suitable for the construction (or assembly) of the various substrates implemented in such a product. The invention also relates to said process of a laminate manufacturing and to the corresponding assembly product.

Hot melt adhesives (or HMA) typically exist as a solid mass at ambient temperature and can be converted to a flowable liquid by the application of heat. These adhesives are particularly useful in manufacturing a variety of disposable products where bonding of various substrates is often necessary.

Specific applications include disposable diapers, hospital pads, feminine sanitary napkins, panty shields, surgical drapes and adult incontinent briefs, collectively known as disposable nonwoven hygiene products. Other diversified applications involve paper products, packaging materials, automotive headliners, appliances, tapes, and labels.

In most of these applications, the hot melt adhesive is heated to its molten state and then applied to a substrate, often named as the primary substrate, at a certain amount (also called "add-on level" or "coating weight"). A second substrate, often named as the secondary substrate, is then immediately brought into contact with and compressed against the first. The adhesive solidifies on cooling to form a strong bond.

The major advantage of hot melt adhesives is the absence of a liquid carrier, as would be the case of water or solvent based adhesives, thereby eliminating the costly process associated with solvent removal. Hot-melt adhesives are generally provided in the form of compositions which comprise a thermoplastic polymer and optionally a tackifying resin and a plasticizer.

As a typical example of a disposable nonwoven hygiene product, one may cite a disposable diaper which will conventionally comprise the following components:
- a backsheet which is impermeable to liquids, typically a PolyEthylene backsheet,
- a topsheet which is permeable to liquids and in contact with the baby's body, and
- an absorbent core sandwiched in between.

The absorbent core is usually available in a core wrap, i.e. an envelope around the absorbing material which can be wood pulp fluff and/or Super Absorbent Polymers (or SAP).

This core wrap typically comprises a bottom layer and a top layer, where the bottom layer is bonded with the backsheet and the top layer is bonded with the topsheet. An acquisition/distribution layer can also be present, generally outside the core wrap and is bonded to the top layer of the core wrap and to the topsheet.

Hot melt "construction adhesives" are therefore used for the permanent construction (or assembly) by bonding of the various substrates corresponding to all these components, by means of a laminating process. The corresponding materials are selected among various nonwoven materials or low surface energy thermoplastic films, such as polylactic acid, polyethylene, or polypropylene. Mention may be made, as an example of such permanent assemblies in the case of diapers, of the lamination of a PolyEthylene (PE) sheet with a nonwoven cloth of PolyPropylene (PP), the latter giving a silky appearance pleasing to the eye and to the touch.

The required level of cohesion for such permanent assemblies (or laminates) is usually quantified by a "peel" and/or a "shear" test.

It is therefore essential that hot melt construction adhesives provide strong peel strength, particularly at low coating weight such as 1 to 3 grams per square meter.

A few components of the diaper are also bonded to the main part of the diaper (also called "chassis"), such as the elastic side panels or the fastening tape, both of which are intended to be attached by means of a closure tape, when the diaper is fixed around the baby's waist. The adhesive joints corresponding to the attachment of these 2 latter components on the main chassis are then submitted to a significant shear stress.

It is therefore important that hot melt construction adhesives also provide an adequate shear strength, particularly at a coating weight comprised in the range from 15 to 30 g/m$^2$.

Most of the commercially available hot melt construction adhesives are based on a Styrenic Block Copolymer (or SBC) as the thermoplastic polymer. Such compositions are well suited to the level of peel strength and shear strength required for the permanent assembly of the various substrates implemented in a disposable nonwoven hygiene product.

The laminating of such substrates (or sheets) is carried out industrially by a process which comprises:
- the heating (to a temperature of between 100 and 250° C. and preferably between 130 and 180° C.) of the hot-melt adhesive composition in a vat (referred to as melting pot or tank), until it becomes molten, then
- the coating of the primary substrate, resulting in the deposition, by means of a nozzle, of a thin layer of said composition in the molten state, and finally
- bringing the primary substrate thus coated into contact, under pressure such as provided for example by nip rolls, with the secondary substrate to be laminated or assembled.

The equipment used for the implementation of such a laminating process is generally a machine (or coater) which operates continuously with often high line speeds and in which, for example, both the components to be laminated or assembled (sheets, films or other substrates) and the final product, often denoted by the term of "complex" or "laminate", are, due to their very large dimensions, packaged by winding off in the form of reels of large width and diameter.

The stage of coating with the melted hot-melt adhesive composition comprises passing it through one or more nozzles at a high pressure, of the order of a few bar to more than 100 bar, so as to obtain good contact (or wetting) with the primary substrate to be coated, which wetting contributes to giving the necessary level of cohesion to the final permanent assembly (or laminate) of the two substrates. The melted hot melt adhesive composition is coated on the primary substrate under the form of a thin layer, the thickness of which is controlled and is generally between 1 and 500 μm. This layer can be either continuous or non-continuous as it can be formed, as an example, by a bead (or fiber) in the case of spiral coating.

In many coating techniques, hot melt adhesives are extruded directly onto the substrate in the form of a thin film or a bead by using piston or gear pump equipment. In this case, the substrate is brought into intimate contact with a hot die under pressure. As the temperature of the die must be maintained well above the melting point of the adhesive to allow the molten hot melt material to flow through the application nozzle smoothly, such direct coating techniques are difficult to implement in the case of delicate and heat sensitive substrates, such as thin gauge plastic films. Such substrates are indeed implemented more and more frequently for manufacturing disposable nonwoven hygiene products.

That is why, besides these directly coating techniques, several indirect or non-contact coating methods are also implemented, through which a hot melt adhesive can be spray coated with the aid of compressed air onto a substrate from a distance. These non-contact coating techniques include spiral spray application such as Summit™ and comb slot application such as Signature™. Summit™ and Signature™ are both available from Nordson.

These indirect methods, however, require that the viscosity of the hot melt adhesive be sufficiently low at the application temperature in order to obtain an acceptable coating pattern. This viscosity may usually be in the range from 2,000 to 20,000 mPa·s, preferably in the range from 2,000 to 15,000 mPa·s and more preferably less than 10,000 mPa·s. Many other physical factors, especially the rheological properties of the adhesive, come into play in determining the applicability (also designated by "processability") of a hot melt by means of a specific nozzle. There are no accepted theoretical models or guidelines to predict processability (for instance "sprayability" in the case of a spiral spray application), which must be determined empirically with the application equipment.

Being "processable" means that the adhesive conforms consistently to a desired applied pattern with minimal loss of adhesive. Consistency of the adhesive pattern on the primary substrate is particularly important in order to ensure homogeneity of the coated adhesive over the surface of said substrate, which is itself an important factor to ensure homogeneity of the required properties of the laminate (such as peel and shear strengths) over its entire surface.

The widely available SBC based hot melt construction adhesives, in addition to providing appropriate levels of peel and shear strength, show a good processability in the various direct or indirect contact equipment.

However, there is a continuing need to decrease the coating temperature in order to use increasingly heat sensitive substrates and/or thinner substrates, while avoiding substrate burning or distortion.

There is also a need to decrease the coating temperature in order to decrease the overall energy consumption of the lamination industrial processes.

SBC based hot melt adhesives do not offer the possibility to further decrease the coating temperature, due to their rheological intrinsic properties. In addition they often provide disposable nonwoven hygiene products with a strong odor, due mainly to the remaining minute amounts of styrene monomers or minutes amounts of isoprene dimers when the SBC is a styrene-isoprene-styrene (SIS) copolymer.

Polyolefin based hot melt adhesives have been developed, which enable to reach a lower coating temperature and which have very low odor level compared with SBC based hot melt adhesives. However, the majority of commercial polyolefin based hot melt adhesives do not lend themselves to spray applications, owing to their poor sprayability and/or processability.

One aim of the present invention is to propose new and improved polyolefin based hot melt adhesives to the manufacturers of disposable nonwoven hygiene products.

Another aim of the present invention is to propose a polyolefin based hot melt adhesive composition which is suitable as a construction adhesive for disposable nonwoven hygiene products.

Another aim of the present invention is to propose a polyolefin based hot melt adhesive composition which provides laminates with adequate peel strength in particular at low coating weights, ranging more particularly from 1 to 3 grams per square meter.

Another aim of the present invention is to propose a polyolefin based hot melt adhesive composition which provides laminates with adequate shear strength in particular at coating weights comprised in the range from 15 to 30 $g/m^2$.

Another aim of the present invention is to propose a polyolefin based hot melt adhesive composition with acceptable levels of peel and shear strengths which are maintained for laminates which have undergone long term or thermally accelerated aging.

Another aim of the present invention is to propose a polyolefin based hot melt adhesive composition which can be implemented in a laminating process at a lower coating temperature.

Another aim of the present invention is to propose a polyolefin based hot melt adhesive composition which has a sufficiently low viscosity at the coating temperature and is sprayable and/or processable at the coating temperature.

Another aim of the present invention is to propose a polyolefin based hot melt adhesive composition which has an adequate sprayability or processability at a lower coating temperature.

It has now been found that the above aims can be achieved in all or in part by means of the hot-melt adhesive composition which is the subject matter of the present invention.

According to a first object of the invention, the present application relates to a hot melt adhesive composition characterized in that it comprises:
  from 30% to 55% of a composition (A) consisting of 2 thermoplastic unimodal copolymers of propylene and ethylene (A1) and (A2), having each a weight average molecular weight (Mw) of less than 100,000 dalton (abbreviated as Da), wherein:
    (A1) is an essentially amorphous copolymer, with a DSC melt enthalpy of less than 30 J/g;
    (A2) is a semicrystalline copolymer with a DSC melt enthalpy of more than 30 J/g; and
    the ratio:weight of (A2)/weight of (A1) is from 0.2 to 1.5;
  from 20% to 50% of a tackifying resin (B); and
  from 2% to 25% of a plasticizer (C) consisting of a liquid polybutene oligomer.

According to an embodiment, the present application relates to a hot melt adhesive composition characterized in that it consists essentially:
  from 30% to 55% of a composition (A) consisting of 2 thermoplastic unimodal copolymers of propylene and ethylene (A1) and (A2), having each a weight average molecular weight (Mw) of less than 100,000 Da, wherein:
    (A1) is an essentially amorphous copolymer, with a DSC melt enthalpy of less than 30 J/g;
    (A2) is a semicrystalline copolymer with a DSC melt enthalpy of more than 30 J/g; and the ratio:weight of (A2)/weight of (A1) is from 0.2 to 1.5;

from 20% to 50% of a tackifying resin (B); and from 2% to 25% of a plasticizer (C) consisting of a liquid polybutene oligomer.

The contents of the above mentioned ingredients (A), (B) and (C) in the hot melt adhesive composition according to the invention are given in percentage by weight and are expressed relatively to the total weight of the hot melt adhesive composition according to the invention.

It has been found that the polyolefin based hot melt adhesive composition according to the invention is well suited to be used as a construction adhesive which can be implemented for the manufacturing of essentially odorless laminates. Said laminates show adequate levels of peel and shear strengths, in particular just as adequate as SBC based HMA, and also show adequate levels of peel after thermally accelerated aging. In said manufacturing processes, the HMA according to the invention also provides just as good a processability as SBC based HMA, while enabling advantageously a significantly lower coating temperature.

Composition (A) Consisting of (A) and (A2):

The hot melt adhesive composition according to the invention comprises from 30% to 55% by weight of the composition (A) consisting of (A1) and (A2).

(A1) and (A2) are each unimodal copolymers of propylene and ethylene, meaning that each of (A1) and (A2) does not constitute a blend or mixture of two polymers or of two different grades of the same polymer. For example, the unimodal (A1) copolymer is not a mixture of two copolymers having different average molecular weights. Stated another way, the unimodal (A1) copolymer is the result of a single process for making a polymer and not a mixture of two different polymers or two different grades of the same polymer (i.e., the same polymer with two different average molecular weights). Therefore, the properties, such as molecular weight, of each of (A1) and (A2) generally have bell-shaped curves. The unimodal nature of for instance (A1) exists for all of its properties, such as comonomer content, heat of fusion, crystallinity, branching index, melting point, glass transition temperature, density, and polydispersity, in addition to molecular weight.

(A1) and (A2) are random copolymers of propylene and ethylene having from about 70% by weight to about 99% by weight of propylene (also abbreviated as PP), preferably from about 80% by weight to about 98% by weight, and most preferably from about 85% by weight to about 98% by weight.

According to a preferred embodiment, (A1) and (A2) are prepared using suitable single-site catalyst systems (abbreviated as "SSC").

Single-site catalyst systems differ from the conventional Ziegler-Natta catalysts in at least one significant way. They have only a single active transition metal site for each catalyst molecule and the activity at this metal site is therefore identical for all the catalyst molecules. One type of SSC catalyst that has now been widely used on industrial scale is a metallocene catalyst system consisting of a catalyst and a co-catalyst or activator. The catalyst is a transition metal complex having a metal atom situated between two cyclic organic ligands; the ligands being the same or different derivatives of cyclopentadiene. The co-catalyst can be any compound capable of activating the metallocene catalyst by converting a metallocene complex to a catalytically active species and an example of such compound is alumoxane preferably methylalumoxane having an average degree of oligomerization of from 4-30.

Single-site catalyst systems for olefin polymerization, including metallocene catalyst systems for copolymerization of ethylene and propylene, are well known to those skilled in the art and are extensively discussed in two symposia entitled Stereoselective Polymerization with Single-Site Catalysts edited by Lisa S. Baugh and Jo Ann M. Canich published by CRC press (2008), and Polyolefins: 50 Years after Ziegler and Natta II: Polyolefins by Metallocenes and Other Single-Site Catalysts edited by Walter Kaminsky and published by Springer Heidelberg (2013). Reference can also be made to U.S. Pat. No. 9,109,143.

The advancement of SSC catalyst systems herein discussed above has made it practical to produce propylene based polymers and copolymers having various chain microstructures and specific stereochemistry. Depending on the choice of catalyst and reaction conditions, specific types of propylene polymers and copolymers, for example, can be purposely made to have narrow molecular weight distribution, statistically random comonomer incorporation, high fraction of atactic chain sequences and shorter crystallizable isotactic or syndiotactic chain sequences. Macroscopically, the polymers exhibit low melting point, low enthalpy of melting, low crystallinity, and low density and behave more similar to elastomers than to conventional polypropylene. Such polymers have various weight average molecular weights (Mw) ranging from 1,000 g/mol to 1,000,000 g/mol, having a melting point between 20° C. to 150° C. which is well below the melting point 170° C. of iPP, having an enthalpy of melting between 0 J/g and 100 J/g and having a density between 0.85 g/cm$^3$ and 0.90 g/cm$^3$, have been produced.

In polymer scientific nomenclature, the term tacticity is used to describe chain configuration, i.e., the stereo structure of a polymer chain. A polymer is called isotactic if it has a chain configuration described as having the radical groups attached to the tertiary carbon atoms of successive monomeric units on the same side of a hypothetical plane drawn through the main polymer chain. This type of stereochemistry structure can be illustrated graphically by:

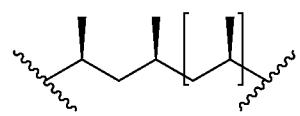

Polypropylene having this type of chain configuration is known as isotactic polypropylene, or iPP.

A polypropylene chain can also adopt syndiotactic configuration in which the tertiary methyl groups of successive monomer units along the chain is alternatively disposed on each side of the hypothetical plane. The stereo configuration of syndiotactic chain can be depicted below:

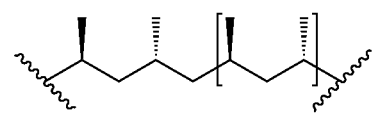

Polypropylene having this type of chain configuration is called syndiotactic polypropylene, or sPP.

In contrast to a regular spatial configuration, a propylene polymer chain can also have a chain stereo structure characterized by having the methyl groups on the successive monomeric units sterically randomly distributed on both sides of the hypothetical plane through the polymer chain. This chain configuration is defined as atactic. The stereo configuration of the atactic polypropylene (aPP) molecular chain can be illustrated graphically by:

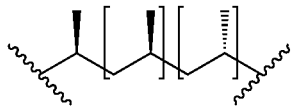

According to a preferred embodiment of the HMA according to the invention, each of (A1) and (A2) include in the chain an isotactic polypropylene chain sequence.

(A1) and (A2) each have a weight average molecular weight (Mw) of less than 100,000 g/mole.

The weight average molecular weight of (A1) is preferably from about 5,000 to 60,000 Da, more preferably from about 20,000 to about 55,000 Da, even more preferably from about 30,000 to about 52,000 Da, still more preferably from about 35,000 to about 50,000 Da, and most preferably from about 40,000 to about 48,000 Da.

The weight average molecular weight of (A2) is preferably from about 10,000 g/mole to about 100,000 Da, more preferably from about 10,000 Da to about 80,000 Da, even more preferably from about 10,000 Da to about 60,000 Da, and most preferably from about 15,000 Da to about 35,000 Da.

Weight average molecular weight is characterized using a High Temperature Size Exclusion Chromatograph (SEC) using a polystyrene reference standard.

According to another preferred embodiment of the HMA according to the invention, (A1) and (A2) each have a melt flow index (MFI) per ASTM D 1238 at 190° C./2.16 kg test conditions of more than 35 g/10 min, preferably from about 35 g/10 min to about 100 g/10 min, more preferably from about 35 g/10 min to about 60 g/10 min.

According to another preferred embodiment of the HMA according to the invention, (A1) and (A2) each have a density at 23° C. measured according to ASTM D1505 of about 0.85 g/cm$^3$ to about 0.90 g/cm$^3$, preferably of about 0.86 g/cm$^3$ to about 0.88 g/cm$^3$.

The composition (A) comprised in the HMA according to the invention consists of an essentially amorphous copolymer (A1) and a semicrystalline copolymer (A2).

For the purposes of the present invention, the term essentially amorphous is used to refer to a state wherein a PP based polymer exhibits a melt enthalpy from 0 J/g to about 30 J/g.

For the purposes of the present invention, the term semicrystalline is used to refer to a state wherein a PP based polymer exhibits a melt enthalpy above 30 J/g.

Copolymers (A1) and (A2) differ essentially in enthalpy of melting, which is an indirect measure of polymer crystallinity.

The essentially amorphous copolymer (A1) contains either no or essentially no crystal phase or a small fraction of residue crystallinity that is characterized by a small, but noticeable melting peak or peaks on a differential scanning calorimetry (DSC) curve with a melt enthalpy below 30 Joules per gram of material (J/g). The essentially amorphous copolymer (A1) may also be completely amorphous showing no melting peak on its DSC curve.

As used herein, DSC curve refers to a plot of heat flow or heat capacity versus temperature obtained by using differential scanning calorimetry (DSC) instrument. The test method used to determine these values is ASTM E793-01 "Standard Test Method for Enthalpies of Fusion and Crystallization by Differential Scanning Calorimetry".

The semicrystalline copolymer (A2) is a PP based copolymer having a distinct melting peak or peaks on a DSC curve with associated enthalpy of melting of 30 joules per gram of material (J/g) or greater, i.e. typically from about 30 J/g to about 100 J/g, more preferably from about 30 J/g to about 90 J/g, and most preferably about 35 J/g to about 80 J/g. The terms "melt enthalpy", "enthalpy of melting", "enthalpy of fusion", "heat of fusion" and "heat of melting" are used interchangeably.

Essentially amorphous and semicrystalline copolymers of propylene and ethylene which can be used as copolymers (A1) and (A2) are also available commercially.

As an example of copolymer (A1), Vistamaxx™ 8380, obtained from Exxonmobil Chemical Company, Houston, Texas, is an essentially amorphous PP based copolymer containing about 12% by weight of ethylene comonomer and having a weight average molecular weight (Mw) of about 43,000 Da, a DSC melting point of about 100° C., a DSC melt enthalpy of about 20 J/g, a density of about 0.864 g/cm$^3$ at 23° C. per ASTM D1505.

As an example of copolymer (A2), Vistamaxx™ 8880, also obtained from Exxonmobil Chemical Company, is a semicrystalline PP based copolymer containing about 6% by weight of ethylene comonomer and having a weight average molecular weight (Mw) of about 27,000 Da, a DSC melting point of about 97° C., a DSC melt enthalpy of about 38 J/g, a density of about 0.880 g/cm$^3$ at 20° C. per ASTM D1505.

Both Vistamaxx 8380 and Vistamaxx 8880 are primarily composed of isotactic propylene units with random ethylene distribution.

According to a more preferred embodiment of the HMA according to the invention, the ratio:weight of (A2)/weight of (A1) within the composition (A) is preferably about 0.5.

The total amount of composition (A) used preferably ranges from 35% to 55% by weight, and even more preferably from 40% to 50% by weight, relative to the total weight of the HMA composition according to the invention.

Tackifying Resin (B):

The hot melt adhesive composition according to the invention comprises from 20% to 50% of the tackifying resin (B).

Said tackifying resin(s) (B) may comprise one or several carbon-carbon double bond(s) or may comprise no carbon-carbon double bond. In this latter case, saturated tackifying resin(s) may be prepared by total hydrogenation of the in saturated tackifying resin(s).

The tackifying resin (B) is preferably selected among the following classes:
(a) natural and modified rosins such as, for example, gum rosins, wood rosins, tall-oil rosins, distilled rosins, hydrogenated rosins, dimerized rosins and polymerized rosins;
(b) glycerol and pentaerythritol esters of natural and modified rosins, such as, for example, the glycerol esters of pale wood rosin, the glycerol esters of hydrogenated rosin, the glycerol esters of polymerized rosin, the pentaerythritol esters of pale wood rosin, the pentaerythritol esters of hydrogenated rosin, the pentaerythritol esters of tall oil rosin and the phenolic modified pentaerythritol esters of rosin;
(c) polyterpene resins including hydrogenated polyterpene resins having a Ring and Ball softening point of from about 20° C. to 140° C., the latter polyterpene resins generally resulting from the polymerization of terpene hydrocarbons, such as the monoterpene known as pinene, in the presence of Friedel-Crafts catalysts at moderately low temperatures;
(d) phenolic-modified terpene resins such as, for example, those resulting from the condensation, in an acidic medium, of a terpene and a phenol;
(e) aliphatic (including cycloaliphatic) petroleum hydrocarbon resins (C5) having a Ring and Ball softening point of from about 60° C. to 140° C., said resins resulting from the polymerization of C5-hydrocarbon monomers; and the corresponding hydrogenated derivatives resulting from a subsequent total or partial hydrogenation thereof;
(f) aromatic petroleum hydrocarbons resins (C9) having Ring and Ball softening point of from about 60° C. to 140° C., said resins resulting from the polymerization of C9-hydrocarbon monomers; and the corresponding hydrogenated derivatives resulting from a subsequent total or partial hydrogenation thereof;
(g) aliphatic (including cycloaliphatic) and/or aromatic petroleum resins (C5/C9) having a Ring and Ball softening point of from about 60° C. to 140° C., said resins resulting from the polymerization of C5/C9-hydrocarbon monomers; and the corresponding hydrogenated derivatives resulting from a subsequent total or partial hydrogenation thereof.

As example of C5-hydrocarbon monomers useful to prepare the tackifying resins belonging to class (e) or (g), mention may be made of trans-1,3-pentadiene, cis-1,3-pentadiene, 2-methyl-2-butene, dicyclopentadiene, cyclopentadiene, cyclopentene, and any mixture thereof.

As example of C9-hydrocarbon monomers useful to prepare the tackifying resins belonging to class (f) or (g), mention may be made of vinyltoluenes, dicyclopentadiene, indene, methylstyrene, styrene, methylindenes, and any mixture thereof.

According to a particular embodiment of the invention, a mixture of two or more of the above described tackifying resins is used in the hot melt adhesive composition according to the invention.

The tackifying resin(s) (B) used according to the invention are commercially available.

As example of commercially available tackifying resin(s) (B) belonging to class (a), mention may be made of:
unmodified natural tall oil rosins from KRATON Company sold under the trade names SYLVAROS® (85, 90 and NCY),
the partially hydrogenated rosin from EASTMAN Company sold under the trade name FORALYN® E and the fully hydrogenated rosin from Eastman sold under the trade name FORAL® AX-E,
the dimerized rosin from EASTMAN Company sold under the trade name DYMEREX®.

As example of commercially available tackifying resin(s) (B) belonging to class (b), mention may be made of:
SYLVALITE® RE 100L, a pentaerythritol based tall-oil rosin ester, and
SYLVALITE® RE 85L, a glycerol ester of tall oil rosin, both available from KRATON Company.

As example of commercially available tackifying resin(s) (B) belonging to class (c), mention may be made of:
the polyterpene tackifiers from KRATON Company sold under the trade names SYLVAGUM® TR and SYLVARES® TR series (7115, 7125, A25L, B115, M1115).

As example of commercially available tackifying resin(s) (B) belonging to class (d), mention may be made of:
the terpene phenol resins from KRATON Company sold under the trade names SYLVARES® TP (96, 2040, 300, 7042, 2019).

As example of commercially available tackifying resin(s) (B) belonging to class (e), mention may be made of:
the aliphatic and cycloaliphatic petroleum hydrocarbon resins based on a C5-petroleum hydrocarbon fraction (such as a mixture of trans-1,3-pentadiene, cis-1,3-pentadiene, 2-methyl-2-butene, dicyclopentadiene, cyclopentadiene, cyclopentene), having a Ring and Ball softening point ranging from 60° C. to 140° C., from EASTMAN Company sold under the trade names WINGTACK® 98, WINGTACK® ET and from EXXONMOBIL sold under the trade name ESCOREZ® 1310LC, and the corresponding fully hydrogenated resins from EASTMAN Company sold under the trade name Eastotac® H100W (softening point of 108° C.).
the partially aliphatic and cycloaliphatic petroleum hydrocarbon resins based on a C5-petroleum hydrocarbon fraction (such as a mixture of trans-1,3-pentadiene, cis-1,3-pentadiene, 2-methyl-2-butene, dicyclopentadiene, cyclopentadiene, cyclopentene), having a Ring and Ball softening point ranging from 80° C. to 140° C., from KOLON Company sold under the trade names SUKOREZ® SU210 and SUKOREZ® 230. The softening point of SUKOREZ® SU210 is 110° C.
the fully hydrogenated cycloaliphatic petroleum hydrocarbon resins based on a dicyclopentadiene-petroleum hydrocarbon fraction, having a Ring and Ball softening point ranging from 60° C. to 140° C., from EXXONMOBIL sold under the tradename ESCOREZ® 5400 series (5400, 5415, 5490). The softening point of ESCOREZ® 5400 is 100° C.

As example of commercially available tackifying resin(s) (B) belonging to class (f), mention may be made of:
the aromatic petroleum hydrocarbon resins based on a C9-hydrocarbon petroleum fraction (such as a mixture of vinyltoluenes, dicyclopentadiene, indene, methylstyrene, styrene, methylindenes), having a Ring and Ball softening point of from about 60° C. to 140° C., available from KOLON INDUSTRIES sold under the trade names HIKOTACK® (P-90, P110 S and P120 S).

As example of commercially available tackifying resin(s) (B) belonging to class (g), mention may be made of:
the partially hydrogenated cycloaliphatic modified aromatic petroleum hydrocarbon resins based on C5/C9-hydrocarbon petroleum fractions, having a Ring and Ball softening point of from about 60° C. to 140° C., from EXXONMOBIL Company sold under the tradename ESCOREZ® 5600 series (5600, 5615, 5690) or from KOLON sold under the tradename Sukorez®NX700. The softening point of ESCOREZ® 5600 and Sukorez®NX700 is 100° C.
the non hydrogenated aliphatic modified aromatic hydrocarbon petroleum resin based on C5/C9-hydrocarbon petroleum fractions sold by ZEON under the trade name QUINTONE® DX390N, with a softening point of 93° C.

According to a preferred embodiment, the Ring and Ball (or softening point) of the tackifying resin(s) (B) preferably lies in the range from 90° C. to 125° C., and even more preferably in the range from 90° C. to 115° C.

The softening temperature (or point) is determined in accordance with the standardized ASTM E 28 test, the principle of which is as follows. A brass ring about 2 cm in diameter is filled with the resin to be tested in the melt state. After cooling to room temperature, the ring and the solid resin are placed horizontally in a thermostated glycerol bath, the temperature of which may vary by 5° C. per minute. A steel ball about 9.5 mm in diameter is centered on the solid resin disk. The softening temperature is, during the rise in temperature of the bath at a rate of 5° C. per minute, the temperature at which the resin disk flows by an amount of 25.4 mm under the weight of the ball.

The total amount of tackifying resin(s) (B) used according to the invention preferably ranges from 25% to 45% by weight, and more preferably from 30% to 40% by weight, relative to the total weight of the hot melt adhesive composition.

Plasticizer (C):

The hot melt adhesive composition according to the invention comprises from 2% to 25% by weight, preferably from 15% to 25% of at least one plasticizer (C) which is a liquid polybutene oligomer.

According to an embodiment, said polybutene (C) is a liquid oligomer of one or more monomer units selected among 1-butene, 2-butene and isobutene.

According to a more preferred embodiment, said polybutene (C) has a kinematic viscosity at 100° C. which is less than about 10,000 centistoke (cSt), preferably 5,000 cSt.

The kinematic viscosity is measured in accordance with D-445 ASTM test method.

Such a plasticizer is available commercially, for instance from INEOS as:

Indopol® H2100, which has a kinematic viscosity at 100° C. of 4,300 cSt, or

Indopol® H100, which has a kinematic viscosity at 100° C. of 215 cSt.

Optional Ingredients:

Antioxidant (D):

Preferably, the hot melt adhesive composition according to the invention comprises from 0.1% to 2% by weight of at least one antioxidant (D), relative to the total weight of the hot melt adhesive composition.

The antioxidant (D) useful according to the invention is preferably incorporated in the hot melt adhesive composition to help protect the hot melt adhesive composition from chemical degradations. Said degradations generally involve the reactions of free radicals, resulting from chain scission catalyzed either by ultraviolet light or heat, with dioxygen. Such degradation is usually manifested by a deterioration in the appearance (browning of color) or other physical properties of the adhesive, and in the performance characteristics of the adhesive.

In particular, the antioxidant(s) (D) protects the adhesive from the effect of thermal degradations reactions which mainly occur during the manufacturing and application process of the adhesive where the hot melt adhesive composition and its ingredients are heated for a long time at high temperature in presence of dioxygen.

Useful antioxidant(s) (D) include hindered phenols and sulfur and phosphorus containing phenols. Hindered phenols are well known to those skilled in the art and may be characterized as phenolic compounds which also contain sterically bulky groups in close proximity to the phenolic hydroxyl group thereof. In particular, tertiary butyl groups generally are substituted onto the benzene ring in at least one of the ortho positions relative to the phenolic hydroxyl group.

Representative hindered phenols include:

1,3,5-trimethyl-2,4,6-tris(3-5-di-tert-butyl-4-hydroxybenzyl) benzene;

pentaerythritol tetrakis-3(3,5-di-tert-butyl-4-hydroxyphenyl) propionate;

n-octadecyl-3(3,5-ditert-butyl-4-hydroxyphenyl) propionate;

4,4'-methylenebis(4-methyl-6-tert-butylphenol);

4,4'-thiobis(6-tert-butyl-o-cresol);

2,6-di-tert-butylphenol;

6-(4-hydroxyphenoxy)-2,4-bis(n-octylthio)-1,3,5-triazine;

2,4,6-tris(4-hydroxy-3,5-di-tert-butyl-phenoxy)-1,3,5-triazine;

di-n-octadecyl-3,5-di-tert-butyl-4-hydroxybenzylphosphonate;

2-(n-octylthio)ethyl-3,5-di-tert-butyl-4-hydroxybenzoate;

sorbitol hexa-(3,3,5-di-tert-butyl-4-hydroxy-phenyl) propionate;

2,2'-methylene bis(4-methyl-6-tert-butylphenol)phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP);

tetrakis(methylene(3,5-di-ter-butyl-4-hydroxyhydrocinnamate)) methane; (tris(2,4-ditert-butylphenyl)phosphate), and combinations thereof.

The hindered phenol antioxidants may be used by themselves or in combination with other antioxidants, such as phosphites antioxidants like IRGAFOS® series, or aromatic amine antioxidants like NAUGARD® series from ADDIVANT.

Useful antioxidants (D) are commercially available under a variety of trade designations including, e.g., the hindered phenolic antioxidants of IRGANOX® series from BASF including, e.g., IRGANOX® 1010 (tetrakis(methylene(3,5-di-ter-butyl-4-hydroxyhydrocinnamate)) methane), and IRGAFOS® 168 antioxidant (tris(2,4-ditert-butylphenyl) phosphate).

The total amount of antioxidant(s) (D) is preferably ranging from 0.1 to 3% by weight, and more preferably from 0.5% to 1% by weight, relative to the total weight of the hot melt adhesive composition.

The performance of the antioxidants useful according to the invention may be further enhanced by utilizing, in conjunction therewith: (1) synergists such as, for example, thiodipropionate esters and phosphites; and/or (2) chelating agents and metal deactivators as, for example, ethylenediamine tetraacetic acid, salts thereof, and disalicylalpropylenediimine.

Other optional ingredient(s) may be incorporated into the hot melt adhesive composition according to the invention in order to modify some of its physical properties.

Among the optional ingredients, mention may be made of fillers, surfactants, colorants, ultraviolet light stabilizers, fluorescent agents, rheology modifiers, and the like.

The total amount of these optional ingredient(s) may range from 0% to 10% by weight, preferably from 0.1% to 5% by weight, and more preferably from 0.1% to 2% by weight, relative to the total weight of the hot melt adhesive composition.

According to a preferred embodiment, the hot melt adhesive composition according to the invention has a Brookfield viscosity measured at 135° C. in the range of from 1,000 mPa·s to 10,000 mPa·s, preferably from 2,000 to 8,000, more preferably from 2,500 to 6,000. The Brookfield viscosity is measured in accordance with ASTM D-3236 using a Brookfield Thermosel viscometer and a number 27 spindle. The spindle speed was adjusted so that the percent torque was between 45% and 90%. The results are reported in milliPascal·seconde (mPa·s).

According to another preferred embodiment, the hot melt adhesive composition according to the invention comprises, and preferably consists essentially of:

a) from 35% to 55% by weight of the composition (A) consisting of copolymers (A1) and (A2), more preferably from 40% to 50%, wherein the ratio:weight of (A2)/weight of (A1) within the composition (A) is preferably about 0.5;
b) from 30% to 40% by weight of the tackifying resin (B); and
c) from 15% to 25% by weight of the plasticizer (C).

According to a second object of the invention, the present application relates to a process of manufacture of the hot melt adhesive composition according to the invention comprising at least a step of mixing and heating at a temperature ranging from 140° C. to 170° C. the ingredients of the hot melt adhesive composition according to the invention, at least for a period of time long enough to melt the tackifying resin(s) (B) and the thermoplastic polymers (A1) and (A2).

The hot melt adhesive composition of the present invention may be produced using any of the techniques known in the art. The ingredients used are preferably mixed and heated at high temperature for at least several hours, typically at least 4 hours, and preferably from 4 to 6 hours, at a temperature ranging from 140 to 170° C.

The hot melt adhesive composition according to the invention can be prepared in presence of dioxygen (such as under air atmosphere), or preferably under inert atmosphere e.g. under carbon dioxide or nitrogen to limit potential degradation by oxidative reactions.

According to a preferred embodiment, the process to manufacture the hot melt adhesive composition according to the invention comprises:
 a first step of mixing and heating the tackifying resin(s) (B), and the plasticizer(s) (C), preferably with the antioxidant(s) (F) when present, at a temperature ranging from 120° C. to 140° C., at least for a period of time long enough to melt all the tackifying resin(s) (B),
 a second step of adding the thermoplastic polymers (A1) and (A2) into the mixture obtained in the previous step under stirring and heating at a temperature ranging from 150° C. to 170° C., at least for a period of time long enough to melt all the thermoplastic polymers.

Additionally, the process of the invention may comprise a step of applying vacuum to remove any entrapped air in the mixture, before or after any of the step of process described previously.

Other useful optional ingredient(s) which may be present in the hot melt adhesive composition according to the invention may be added at any step of the process according to the invention.

The hot melt adhesive composition according to the invention, prepared by the above-described process may further be kept, for example in a melting kettle, under melted state for up to an additional 15 hours before being cooled down and packaged in form of a ready-to-use solid composition.

According to a third object of the invention, the present application relates to a process of manufacturing an assembly product (or laminate) comprising:
 a step (i) of heating at a temperature ranging from 130° C. to 180° C. the hot melt adhesive composition according to the invention, for at least a period of time long enough to render the hot melt adhesive composition liquid enough to be applied on a substrate (for example at least two hours at industrial scale), then
 a step (ii) of coating said composition on a primary substrate, then
 a step (iii) of putting into contact the coated surface of the primary substrate with the surface of a secondary substrate, so as to form an adhesive joint bonding the two substrates.

The substrates may be different or of same nature, with various forms (layer or film, strands, fluff)

Preferably each substrate may be chosen independently from one another among nonwoven fabric, tissue, absorbent fluff, super absorbent polymer (SAP), composite material, plastics which may be elastomeric or non elastomeric, and which may be chosen for example from Styrene Block Copolymers (SBC), Polyurethane, and Polyolefin, and any mixture thereof. The composite material may be made of at least one of the above-mentioned materials. A nonwoven fabric is defined as an interlocking fiber network characterized by flexibility, porosity and integrity. The individual fibers used to compose the nonwoven fabric may be synthetic, naturally occurring, or a combination of the two. The individual fibers may be mechanically, chemically or thermally bonded to each other.

The hot melt adhesive composition according to the invention can be coated or applied with a variety of application techniques known in the art, which include contact type application (such as slot die coating) and non-contact type application (such as spraying, fiberization or comb slot application).

In particular, as mentioned above, the hot melt adhesive composition according to the invention can be applied easily through conventional coating nozzles, such as those having a diameter from 0.305 to 0.762 mm or a slot die length adjustable by a shim and ranging from 20 µm to 300 µm.

The amount of coated adhesive by surface unit can vary in a very large range from 0.1 to 50 g/m², depending on the substrates intended to be bonded. For example one may cite a range from 0.2 to 1 g/m² in case of nonwoven substrates bonded with the polyethylene film to produce a cloth-like backsheet assembly, while a range from 3 to 7 g/m² can be used in case of the assemblies of the disposable multilayers. A much higher range, from 20 to 40 g/m², can also be used when high shear performance is requested, like for instance for bonding the elastic side panels or the fastening tapes to the diaper chassis.

Before being applied on the surface of the primary substrate, the hot melt adhesive composition according to the invention may further be kept in a melting kettle for up to 4 days.

The hot melt adhesive composition according to the invention can be applied on a substrate or stored in presence of dioxygen (under air atmosphere), or preferably under inert atmosphere to limit degradations due to oxidative reactions.

According to a fourth object of the invention, the present application relates to an assembly product comprising at least two substrates bonded by at least one hot melt adhesive composition according to the invention.

The substrates bonded may be chosen among the substrates listed above for the process of applying the hot melt adhesive composition, according to the invention.

The hot melt adhesive composition according to the invention may be used as the laminating adhesive to bind a plurality of substrate layers for example to manufacture toilet tissues, paper towels, wipes and other consumer products, particularly absorbent articles such as disposable hygiene products, and more particularly disposable diapers.

In a particular embodiment of the invention, the assembly product according to the invention may be a multilayer product comprising at least two layers of substrate(s) bonded by at least one hot melt adhesive composition according to the invention.

In the assembly product according to the invention, the at least two layers of substrate(s) may be joined adhesively by a layer of hot melt adhesive composition according to the invention, in sandwich between the two layers of substrate(s).

Alternatively or cumulatively, the at least two layers of substrate(s) may be joined adhesively by spots of hot melt adhesive composition according to the invention.

Preferably, the assembly product is a disposable nonwoven absorbent article.

The following examples are given purely by way of illustration of the invention and should not, under any circumstances, be interpreted as limiting the scope thereof.

EXAMPLE A (REFERENCE): SBC BASED HMA AND LAMINATE OBTAINED THEREFROM

A1—Preparation of the HMA:

The composition of example A in Table 1 is prepared by simple mixing of its ingredients as pointed out above in the detailed description of the invention.

Its Brookfield viscosity at 135° C. is measured as above and also reported in Table 1.

A2—Preparation of a Laminate A2 by Means of a Spiral Spray Summit™ Coating Equipment:

A laminate A2 is prepared as follows.

Use is made, as a laminating device, of a machine operating continuously at a line speed of approximately 400 m/minute, which machine is sold by NORDSON under the name of Coater CTL 4400.

In this machine, the coating nozzle is a spiral spray nozzle (NORDSON Summit™).

The two substrates employed are:
- a 20 μm thick breathable PE film which was previously Corona treated on one side, and which has a width of 20 cm, and
- a 16 g/m² spunbond hydrophobic nonwoven sheet of the same width, which is composed of fibers of polypropylene (PP).

These two substrates are packaged as a reel with a width of 20 cm.

The composition of example A is heated in the melting pot at a temperature of 155° C.

It is then coated on the untreated side of the PE film at the same temperature of 155° C. and at a coating weight of approximately 3 g/m².

The resulting coating pattern is quite adequate and is typical of a good sprayability (and processability). It corresponds to a 2.54 cm wide non continuous layer which is made of an offset spiralled filament, which is centered on said PE film and along an axis which is perpendicular to the axis of the reel.

Then, at about 0.25 s after coating (open time), the nonwoven (PP) sheet is put into contact with the coated surface of the PE film, by means of a nip roll applying a pressure of 1 bar.

A3—Peel Measured Initially and after Aging at 23° C. and at 55° C., for Laminate A2:

The laminate A2 obtained is then packaged as a reel and left for 24 hours at ambient temperature and at 50% relative humidity.

A rectangular strip measuring 2.54 cm by approximately 10 cm is then cut out in the coated central area of the laminate.

The two individual substrates are separated, starting from one end of the above rectangular strip (as a test specimen) and over approximately 2 cm.

The two free ends thus obtained are fixed to two clamping devices respectively connected to a stationary part and a movable part of a tensile testing device which are located on a vertical axis.

While a drive mechanism communicates, to the movable part, a uniform speed of 300 mm/minute, resulting in the separation of the two substrates, the separated ends of which are gradually displaced along a vertical axis while forming an angle of 180°, the stationary part, connected to a dynamometer, measures the force withstood by the test specimen thus held.

The result corresponding to the peel after 24 hours at 23° C. (also called "initial peel"), is expressed in N.

The peel after, respectively, 2 weeks at 23° C. and 4 weeks at 23° C., is measured by repeating the above protocol except that the assembly obtained after lamination is aged during the respective time at 23° C.

The peel after, respectively, 2 weeks at 55° C. and 4 weeks at 55° C., is measured by repeating the above protocol except that the assembly obtained after lamination is aged during the respective time at 55° C.

The results are reported in Table 2 below.

A4—Preparation of a Laminate by Means of a Comb Slot Signature™ Coating Equipment:

A laminate A4 is prepared by repeating the protocol A2 above, except that the Spiral spray Summit™ coating equipment is replaced by a comb slot Signature™ coating equipment.

The coating pattern obtained after coating at 155° C. the PE film is typical of a good processability. It corresponds to a 2.54 cm wide non continuous layer which comprises a multiplicity of homogeneously scattered adhesive filaments of variable length. Said non continuous layer is centered on said PE film and along an axis which is perpendicular to the axis of the reel.

A5—Peel Measured Initially and after Aging at 23° C. and 55° C., for Laminate A4:

The protocol of A3 above is repeated for laminate A4.

The results are reported in Table 3.

A6—Shear Test on a Laminate A6 Comprising 2 Non Woven PP:

The level of cohesion of the laminate is also assessed by the shear test, the principle of which consists of the determination of the force necessary for the separation by shear of two substrates bonded by the adhesive composition.

A6.1 Preliminary Preparation of a Laminate A6 Bonded by the Adhesive Composition of Example A:

Use is made, as a laminating device, of a machine operating continuously at a line speed of approximately 100 m/minute, which machine is sold by NORDSON under the name of Coater CTL 4400.

In this machine, the coating nozzle is a slot nozzle, NORDSON Slot™.

The two substrates employed are identical and consist of a 40 g/m² melt blown nonwoven sheet with a width of 20 cm composed of fibers of polypropylene (PP).

These two identical substrates are packaged as a reel with a width of 20 cm.

The adhesive composition of example A is heated in the melting pot at a temperature of 155° C., then is coated on 2 cm from the right edge of the first substrate, resulting in the deposition over said edge of a continuous layer with a width of 1.5 cm corresponding to an amount of approximately 20 g/m², which layer is positioned perpendicular to the axis of the reel.

The second substrate is then laminated over the first coated substrate, with an open time of about 0.5 s, by means of a nip roll applying a pressure of 1 bar, in such a way that the adhesive layer is 2 cm from its left edge.

A6.2 Shear:

The laminate obtained is then packaged as a reel and left for 24 hours at ambient temperature and at 50% relative humidity.

The laminated substrates with a total width of about 35 cm and assembled by the 1.5 cm wide coated region are then cut out in the cross direction, so as to obtain a test specimen of rectangular shape with a length of approximately 35 cm and a width of 2.54 cm.

The first substrate of the specimen is then hung secure in an oven at 38° C., while a 500 g weight is attached to the secondary substrate.

The time after which the assembly fails, corresponding to the shear after 24 hours at ambient temperature, was found to be equal to 29 minutes.

A7—Preparation of a Laminate A7 by Means of a Spiral Spray Summit™ Coating Equipment:

A laminate A7 is prepared as follows.

Use is made, as a laminating device, of a machine operating continuously at a line speed of approximately 200 m/minute, which machine is sold by NORDSON under the name of Coater CTL 4400.

In this machine, the coating nozzle is a spiral spray nozzle (NORDSON Summit™).

The two substrates employed are:
a 20 µm thick breathable PE film which has a width of 20 cm, and
a 16 g/m² spunbond hydrophilic nonwoven sheet of the same width, which is composed of fibers of polypropylene (PP).

These two substrates are packaged as a reel with a width of 20 cm.

The composition of example A is heated in the melting pot at a temperature of 155° C.

It is then coated on the PE film at the same temperature of 155° C. and at a coating weight of approximately 3 g/m².

The resulting coating pattern is quite adequate and is typical of a good sprayability (and processability). It corresponds to a 2.54 cm wide non continuous layer which is made of an offset spiralled bead, which is centered on said PE film and along an axis which is perpendicular to the axis of the reel.

Then, at about 0.5 s after coating (open time), the nonwoven (PP) sheet is put into contact with the coated surface of the PE film, by means of a nip roll applying a pressure of 1 bar.

A8—Peel Measured Initially and after Aging at 23° C. and 55° C., for Laminate A7:

The protocol of A3 above is repeated for laminate A7.
The initial peel is reported in Newton in Table 4.
The peel after storage of, respectively, 1 week at 55° C., 2 weeks at 55° C. and 4 weeks at 55° C. are converted into the relative value of variation of peel versus the initial peel and expressed in % in Table 4.

Example 1 (According to the Invention)

1. Preparation of the HMA:
The composition of example 1 reported in Table 1 is prepared as for the composition of example A.

Its Brookfield viscosity at 135° C. is measured and reported in Table 1.

2. Peel Measured Initially and after Aging at 23° C. and at 55° C., for Laminate A2:

A laminate A2 obtained through Summit™ coating equipment is prepared by repeating the protocol A2 of example A, except that:
the coating composition is replaced by the composition of example 1; and
the coating temperature of 155° C. is replaced by a coating temperature of 130° C. or 145° C.

For each of these 2 coating temperatures, the resulting coating pattern is just as adequate as the one obtained for the reference example A, and is also typical of a good sprayability (and processability).

The peels measured initially and after aging at 23° C. and 55° C. are determined on the laminate corresponding to each of the 2 coating temperatures of 130° C. and 145° C., by repeating the protocol A3 above.

The results are reported in Table 2.

While peel values greater than 1 N are already quite acceptable, these results show that excellent peels values, greater than 2 N, are obtained, both initially and after 2 or 4 weeks storage at 23° C., for the laminate A2 comprising the HMA of Example 1. These values are at least just as good as those of the laminate A2 comprising the reference SBC based HMA of Example A. These levels are also obtained together with an adequate sprayability (or processability) and, most advantageously, they are achieved at coating temperatures of 130° C. and 145° C., which are well below the coating temperature of 155° C. required for Example A.

As to the peels obtained after storage at a temperature of 55° C., most of the results are still greater than about 1 N. These values are to be construed as an indicator of the HMA ability to withstand extended storage over time and under variable storage temperatures. On the whole, the peel values for the HMA of Example 1 are quite comparable with those for the reference SBC based HMA of Example A, taking also into account the much lower coating temperatures of 130° C. and 145° C., with respect to the 155° C. coating temperature for Example A.

3. Peel Measured Initially and after Aging at 23° C. and 55° C., for Laminate A4:

A laminate A4 obtained through Signature™ coating equipment is prepared by repeating the protocol A4 of example A, except that:
the coating composition is replaced by the composition of example 1; and
the coating temperature of 155° C. is replaced by a coating temperature of 130° C. or 145° C.

For each of these 2 coating temperatures, the resulting coating pattern is just as adequate as the one obtained for the reference example A and is also typical of a good processability.

The peels measured initially and after aging at 23° C. and 55° C. are determined on the laminate corresponding to each of the 2 coating temperatures of 130° C. and 145° C., by repeating the protocol A3 above.

The results are reported in Table 3.

While peel values greater than 1 N are already quite acceptable, these results show that good peels values, globally greater than about 1.5 N, are obtained, both initially and after 2 or 3 weeks storage at 23° C., for the laminate A4 comprising the HMA of Example 1. These values are just as good as those of the laminate A4 comprising the reference SBC based HMA of Example A. These levels are also obtained together with an adequate sprayability (or processability) and, most advantageously, they are achieved at coating temperatures of 130° C. and 145° C., which are well below the coating temperature of 155° C. required for Example A.

As to the peels obtained after storage at a temperature of 55° C., most of the results are still greater than about 1 N. These values are to be construed as an indicator of the HMA ability to withstand extended storage over time and under variable storage temperatures. On the whole, the peel values for the HMA of Example 1 are quite comparable with those for the reference SBC based HMA of Example A, taking also into account the much lower coating temperatures of 130° C. and 145° C., with respect to the 155° C. coating temperature for Example A.

4. Shear Test on a Laminate A6:

A laminate A6 is prepared by repeating the protocol A6.1 of example A, except that:
- the coating composition is replaced by the composition of example 1; and
- the coating temperature of 155° C. is replaced by a coating temperature of 130° C.

The time after which the assembly fails, corresponding to the shear after 24 hours at ambient temperature, was found to be equal to 7 hours and 34 minutes, corresponding to a far better shear value with respect to the laminate A6 comprising the HMA of Example A.

5. Peel Measured Initially and after Aging at 23° C. and at 55° C., for Laminate A7:

A laminate A7 is prepared by repeating the protocol A7 of example A, except that:
- the coating composition is replaced by the composition of example 1; and
- the coating temperature of 155° C. is replaced by a coating temperature of 130° C.

The initial peel is reported in Newton in Table 4.

The peel after storage of, respectively, 4 weeks at 23° C. and 4 weeks at 55° C. are converted into the relative value of variation of peel versus the initial peel and expressed in % in Table 4.

Examples 2 and 3 (According to the Invention)

Peel Measured Initially and after Aging at 23° C. and at 55° C., for Laminate A7:

A laminate A7 is prepared by repeating example 1 point 5 with the compositions of examples 2 and 3 shown in table 1.

The initial peel is reported in Newton in Table 4.

The peel after storage of, respectively, 1 week at 55° C., 2 weeks at 55° C. and 4 weeks at 55° C. are converted into the relative value of variation of peel versus the initial peel and expressed in % in Table 4.

The relative loss of peel after aging (versus the initial peel) which is observed is quite comparable to the reference SBC based HMA of Example A.

Example 4 (Comparative)

Peel Measured Initially and after Aging at 23° C. and at 55° C., for Laminate A7

A laminate A7 is prepared by repeating example 1 point 5 with the composition of example 4 shown in table 1.

The initial peel is reported in Newton in Table 4. This peel is about half of the initial peel observed for the examples 2 and 3.

The peel after storage of, respectively, 4 weeks at 23° C., 1 week at 55° C., 2 weeks at 55° C. and 4 weeks at 55° C. are converted into the relative value of variation of peel versus the initial peel and expressed in % in Table 4.

The relative loss of peel after aging (versus the initial peel) which is observed is significantly much more important than for the HMA of examples 1, 2 and 3 according to the invention.

TABLE 1

| | Ingredients | HMA content in ingredient (in % weight) | | | | |
| --- | --- | --- | --- | --- | --- | --- |
| | | Example A (ref.) | Example 1 | Example 2 | Example 3 | Example 4 (comp.) |
| (A1) | KRATON ® D1152 | 18.6 | — | — | — | — |
| (A1) | Vistamaxx ™ 8380 | — | 30.5 | 30.5 | 30.5 | 30.5 |
| (A2) | Vistamaxx ™ 8880 | — | 15.0 | 15.0 | 15.0 | 15.0 |
| (B) | ESCOREZ ® 5400 | 28.7 | — | — | — | — |
| (B) | ESCOREZ ® 5600 | 28.7 | — | — | 17.0 | 39.0 |
| (B) | Sukorez ® NX700 | — | 34.0 | — | — | — |
| (B) | Eastotac ® H100W | — | — | 34.0 | 17.0 | — |
| | Nyflex ® 223* | 23.5 | — | — | — | 15.0 |
| (C) | Indopol ® H100 | — | 20 | 20 | 20 | — |
| (D) | Irganox ® 1010 | 0.5 | 0.5 | 0.5 | 0.5 | 0.5 |
| | Brookfield viscosity at 135° C. (mPa.s) | 5,480 | 3,975 | 4,075 | 4,042 | 3,145 |

*naphtenic oil

TABLE 2

Peel measured initially and after aging at 23° C. and 55° C. for laminates A2 obtained through Summit ™ coating equipement

| | Example A (ref.) | Example 1 | |
| --- | --- | --- | --- |
| Coating temperature of the laminate | 155° C. | 130° C. | 145° C. |
| Processability | adequate | adequate | adequate |
| Initial peel (N) | 2.49 | 2.28 | 2.12 |
| Peel after 2 weeks at 23° C. (N) | 2.06 | 2.39 | 2.66 |
| Peel after 4 weeks at 23° C. (N) | 2.94 | 2.13 | 2.5 |
| Peel after 2 weeks at 55° C. (N) | 1.45 | 1.99 | 2.27 |
| Peel after 4 weeks at 55° C. (N) | 1.41 | 1.72 | 2.04 |

TABLE 3

Peel measured initially and after aging at 23° C. and 55° C. for laminates A4 obtained through Signature ™ coating equipement

| | Example A (ref.) | Example 1 | |
| --- | --- | --- | --- |
| Coating temperature of the laminate | 155° C. | 130° C. | 145° C. |
| Processability | adequate | adequate | adequate |
| Initial peel (N) | 1.53 | 1.62 | 1.44 |
| Peel after 2 weeks at 23° C. (N) | 1.85 | 1.71 | 1.33 |
| Peel after 4 weeks at 23° C. (N) | 1.67 | 2.13 | 2.5 |

TABLE 3-continued

Peel measured initially and after aging at 23° C. and 55° C. for laminates A4 obtained through Signature™ coating equipement

|  | Example A (ref.) | Example 1 |  |
|---|---|---|---|
| Peel after 2 weeks at 55° C. (N) | 1.21 | 1.99 | 2.27 |
| Peel after 4 weeks at 55° C. (N) | 1.16 | 1.72 | 2.04 |

TABLE 4

Peel measured initially and after aging at 23° C. and 55° C. for laminates A7 obtained through Summit™ coating equipement

|  | Example A (ref.) | Example 1 | Example 2 | Example 3 | Example 4 (comparative) |
|---|---|---|---|---|---|
| Coating temperature of the laminate (° C.) | 155° C. | 130° C. | 130° C. | 130° C. | 130° C. |
| Processability | adequate | adequate | adequate | adequate | adequate |
| Initial peel (N) | 1.35 | 1.05 | 1.35 | 1.68 | 0.78 |
| Peel after 4 weeks at 23° C. (%) | N.T.* | +8% | N.T.* | N.T.* | −59% |
| Peel after 1 week at 55° C. (%) | −24% | N.T.* | −23% | −26% | −48% |
| Peel after 2 weeks at 55° C. (%) | −32% | N.T.* | −29% | −33% | −53% |
| Peel after 4 weeks at 55° C. (%) | −37% | −39% | −30% | −41% | −58% |

N.T.* = Not Tested

The invention claimed is:

1. Hot melt adhesive composition comprising:
   from 30% to 55% of a composition (A) comprising 2 thermoplastic unimodal copolymers of propylene and ethylene (A1) and (A2), each having a weight average molecular weight (Mw) of less than 100,000 Da, wherein:
   (A1) is an essentially amorphous copolymer, with a DSC melt enthalpy of less than 30 J/g;
   (A2) is a semicrystalline copolymer with a DSC melt enthalpy of more than 30 J/g; wherein a ratio of weight of (A2)/weight of (A1) is from 0.2 to 1.5;
   from 20% to 50% of a tackifying resin (B); and
   from 2% to 25% of a plasticizer (C) consisting of a liquid polybutene oligomer.

2. Hot melt adhesive composition according to claim 1, wherein (A1) and (A2) are random copolymers of propylene and ethylene having from about 70% by weight to about 99% by weight of propylene.

3. Hot melt adhesive composition according to claim 1, wherein each of (A1) and (A2) include an isotactic polypropylene chain sequence.

4. Hot melt adhesive composition according to claim 1, wherein the weight average molecular weight of (A1) is from about 5,000 to 60,000 Da and the weight average molecular weight of (A2) is from about 10,000 g/mole to about 100,000 Da.

5. Hot melt adhesive composition according to claim 1, wherein (A1) and (A2) each have a melt flow index (MFI) of more than 35 g/10 min.

6. Hot melt adhesive composition according to claim 1, wherein (A1) exhibits a melt enthalpy from 0 J/g to about 30 J/g and (A2) has an enthalpy of melting from about 30 J/g to about 100 J/g.

7. Hot melt adhesive composition according to claim 1, wherein the ratio of weight of (A2)/weight of (A1) within the composition (A) is about 0.5.

8. Hot melt adhesive composition according to claim 1, wherein the tackifying resin (B) is selected among:
   a) natural and modified rosins;
   b) glycerol and pentaerythritol esters of natural and modified rosins;
   c) polyterpene resins;
   d) phenolic-modified terpene resins;
   e) aliphatic petroleum hydrocarbon resins (C5) having a Ring and Ball softening point of from about 60° ° C. to 140° C., and the corresponding hydrogenated derivatives;
   f) aromatic petroleum hydrocarbons resins (C9) having Ring and Ball softening point of from about 60° ° C. to 140° C., and the corresponding hydrogenated derivatives;
   g) aliphatic and/or aromatic petroleum resins (C5/C9) having a Ring and Ball softening point of from about 60° C. to 140° ° C., and the corresponding hydrogenated derivatives.

9. Hot melt adhesive composition according to claim 1, wherein the softening point of the tackifying resin(s) (B) lies in the range from 90° C. to 125° C.

10. Hot melt adhesive composition according to claim 1, wherein polybutene (C) is a liquid oligomer of one or more monomer units selected from the group consisting of 1-butene, 2-butene and isobutene.

11. Hot melt adhesive composition according to claim 1, wherein polybutene (C) has a kinematic viscosity at 100° C. which is less than about 10,000 centistoke.

12. Hot melt adhesive composition according to claim 1, wherein it comprises:
   a) from 35% to 55% by weight of the composition (A) comprising copolymers (A1) and (A2) wherein the ratio of weight of (A2)/weight of (A1) is about 0.5;
   b) from 30% to 40% by weight of the tackifying resin (B); and
   c) from 15% to 25% by weight of the plasticizer (C).

13. Process of manufacturing an assembly product, comprising:
   a step (i) of heating at a temperature ranging from 130° ° C. to 180° C. the hot melt adhesive composition as defined in claim 1, for at least a period of time long enough to render the hot melt adhesive composition liquid enough to be applied on a substrate, then
   a step (ii) of coating said composition on a primary substrate, then
   a step (iii) of putting into contact the coated surface of the primary substrate with the surface of a secondary substrate, so as to form an adhesive joint bonding the two substrates.

14. Assembly product comprising at least two substrates bonded by at least one hot melt adhesive composition such as defined in claim 1.

15. Assembly product according to claim 14, wherein it is a disposable nonwoven absorbent article.

* * * * *